(12) United States Patent
Steger

(10) Patent No.: US 9,474,846 B2
(45) Date of Patent: Oct. 25, 2016

(54) SYSTEM AND METHOD FOR DETECTING VENOUS NEEDLE DISLODGEMENT

(71) Applicant: B. BRAUN AVITUM AG, Melsungen (DE)

(72) Inventor: Jennifer Steger, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 58 days.

(21) Appl. No.: 14/627,330

(22) Filed: Feb. 20, 2015

(65) Prior Publication Data

US 2015/0246173 A1 Sep. 3, 2015

(30) Foreign Application Priority Data

Feb. 28, 2014 (DE) ......................... 10 2014 102 732

(51) Int. Cl.
*A61M 37/00* (2006.01)
*A61M 1/38* (2006.01)
*A61M 1/36* (2006.01)

(52) U.S. Cl.
CPC ............ *A61M 1/38* (2013.01); *A61M 1/3607* (2014.02); *A61M 1/3656* (2014.02); *A61M 2205/13* (2013.01); *A61M 2205/14* (2013.01); *A61M 2205/15* (2013.01); *A61M 2205/17* (2013.01); *A61M 2205/18* (2013.01); *A61M 2205/3344* (2013.01)

(58) Field of Classification Search
CPC ........... A61M 1/3653; A61M 1/3655; A61M 1/3656; A61M 1/3659; A61M 1/3661; A61M 1/3669; A61M 1/3607; A61M 1/38; A61M 2205/13; A61M 2205/14; A61M 2205/15; A61M 2205/17; A61M 2205/18
See application file for complete search history.

(56) References Cited

U.S. PATENT DOCUMENTS 6,090,048 A * 7/2000 Hertz ................ A61M 5/16859
600/485
6,221,040 B1 4/2001 Kleinekofort
(Continued)

FOREIGN PATENT DOCUMENTS

DE 10 2008 015 832 10/2009
DE 10 2008 059 379 6/2010
(Continued)

OTHER PUBLICATIONS

Entire patent prosecution history of U.S. Appl. No. 14/630,797, filed Feb. 25, 2015, entitled, "Apparatus and Method for Detecting Venous Needle Dislodgement."
(Continued)

*Primary Examiner* — Philip R Wiest
(74) *Attorney, Agent, or Firm* — RatnerPrestia

(57) ABSTRACT

Systems and methods are disclosed for detecting an interruption of connection between a blood treatment apparatus and a patient blood circulation. The system includes a line shut-off for blocking the venous fluid line arranged between the blood treatment apparatus and a connector, an arterial fluid line arranged between the blood treatment apparatus and the patient blood circulation, a pressure sensor arranged in the venous fluid line or the arterial fluid line for measuring pressure, and a control and evaluation unit for evaluating a pressure curve in time of the pressure measured by the pressure sensor during blocking of the venous fluid line to detect an interruption or disturbance of the connection between the first connection means and the patient blood circulation.

15 Claims, 8 Drawing Sheets

(56) References Cited

U.S. PATENT DOCUMENTS

| | | |
|---|---|---|
| 6,595,942 B2 | 7/2003 | Kleinekofort |
| 6,595,992 B1 | 7/2003 | Wagner |
| 7,648,474 B2 | 1/2010 | Paolini et al. |
| 2003/0128125 A1 | 7/2003 | Burbank |
| 2008/0065006 A1 | 3/2008 | Roger |
| 2010/0022934 A1* | 1/2010 | Hogard ............... A61M 1/3656 604/5.01 |
| 2011/0034814 A1 | 2/2011 | Kopperschmidt |
| 2011/0230772 A1 | 9/2011 | Koball et al. |
| 2011/0301472 A1 | 12/2011 | Grober et al. |
| 2013/0204174 A1* | 8/2013 | Olde .................. A61M 1/3653 604/6.11 |

FOREIGN PATENT DOCUMENTS

| | | |
|---|---|---|
| DE | 10 2008 061 122 | 6/2010 |
| EP | 1584339 | 10/2005 |
| EP | 2218470 | 8/2010 |
| EP | 2 318 073 | 5/2011 |
| WO | WO 97/10013 | 3/1997 |
| WO | WO 2011/080187 | 7/2011 |
| WO | WO 2012/175267 | 12/2012 |

OTHER PUBLICATIONS

European Search Report for EP 15154748.6 dated Jul. 3, 2015, including partial translation.

European Search Report mailed Jul. 14, 2015 in European Application No. 15154745.2, including partial translation.

German Search Report for DE 10 2014 102 731.0 issued Dec. 10, 2014, including partial translation.

German Search Report for DE 10 2014 102 732.9 issued Dec. 8, 2014.

\* cited by examiner

SYSTEM AND METHOD FOR DETECTING VENOUS NEEDLE DISLODGEMENT

CROSS REFERENCE TO RELATED APPLICATIONS

This application claims priority to German application DE 10 2014 102 732.9 filed Feb. 28, 2014, the contents of such application being incorporated by reference herein.

FIELD OF THE INVENTION

The invention relates to a system and a method for detecting venous needle dislodgement, especially during extracorporeal blood treatment. The extracorporeal blood treatment can be employed when a blood treatment therapy such as hemodialysis, hemofiltration or hemodiafiltration is carried out. As a rule, an apparatus for monitoring a venous vascular access during extracorporeal blood treatment is used.

BACKGROUND

For blood treatment the blood of a patient can be guided via an extracorporeal blood circulation, for example in the course of hemodialysis, hemofiltration or hemodiafiltration. In order to obtain access to the patient's vascular system arteriovenous fistulae, shunts or else vascular implantations can be used. The connection of the extracorporeal blood circulation to the patient is usually made via catheters or cannulas or needles, e.g. dialysis cannulas or needles, by which a fistula or a shunt or, respectively, a vascular implantation, for example, is punctured and a fluid communication is established in this way.

At the beginning of or else during blood treatment the case may occur that the venous access to the blood circulation is disturbed when, for example, the needle or cannula gets out of place and the extracorporeal circulation is no longer connected properly, or is no longer connected at all, to the intracorporeal circulation, i.e. the patient's circulation. This may cause problems especially in the case of disconnection of the venous access from the patient's circulation. Unless such disconnection of the venous access is detected in due time, blood continues being withdrawn from the patient via the arterial access but is no longer properly returned to the patient's body after the extracorporeal blood treatment. In the case of common blood flow rates of 300 to 400 ml/min, for example, a critical situation will develop within few minutes.

DESCRIPTION OF THE RELATED ART

EP 1 584 339 B1 discloses a method based on the measurement of arterial and venous pressures while sums and differences are formed.

In an apparatus according to U.S. Pat. No. 7,648,474 B2 the arterial and venous pressure values are monitored for determining needle dislodgement.

In an apparatus according to DE 10 2008 059 379 A1 for measuring the blood pressure in the arterial vascular access the arterial and venous vascular accesses are shut off during measurement and the blood is returned via a bypass upstream of the venous shut-off and downstream of the arterial shut-off from the venous line to the arterial line.

In an apparatus according to EP 2 318 073 B1 for detecting a needle dislodgement a diaphragm blood pump is employed which alternately includes a flow period and a no-flow period. During the no-flow period the venous pressure drop is evaluated.

In accordance with WO 97/10013 and WO 2011/080187 A1, pressure pulses generated by pulse generators and measured by pressure sensors are evaluated so as to conclude a disconnection failure in the extracorporeal blood circulation.

In accordance with WO 2012/175267 A1, for detecting needle dislodgement signals of an arterial pressure sensor are evaluated with reference to frequency shares which correlate with pressure pulses from pulse generators.

The detection method according to DIN VDE 0753-4 is based on the evaluation of the venous pressure (PV) measured in the extracorporeal blood circulation. Depending on the current venous pressure limits (UCL=upper control limit; LCL=lower control limit) are defined. When the lower limit LCL is underrun, a venous alert comparable to the detection of venous needle dislodgement (VND) is triggered.

SUMMARY OF THE INVENTION

It is an object of the invention to provide a system and a method for detecting venous needle dislodgement which can be employed with high precision for continued extracorporeal blood treatment.

The object is achieved by the features of the independent claims. The dependent claims are directed to preferred embodiments of the invention.

In accordance with the invention, a system for detecting an interruption of the connection between an extracorporeal blood treatment apparatus (dialyser), especially a dialysis machine, and an intracorporeal patient blood circulation is provided to which the extracorporeal blood treatment apparatus is connectable or connected via a fluid communication means, preferably a needle or cannula, attachable or attached to a first venous fluid line, preferably to the line end thereof, and via a second arterial fluid line. Especially a system is provided for detecting slipping of the fluid communication/coupling means, such as a needle or cannula, out of the intracorporeal patient circulation (i.e. an interruption of the connection between the dialyser and the patient circulation on the venous side of the extracorporeal circulation). The system according to aspects of the invention is provided with a line shut-off for (exclusively) blocking the first venous fluid line arranged between the blood treatment apparatus and the fluid communication means (needle, cannula), a pressure sensor arranged in the first venous fluid line and/or the second arterial fluid line for measuring the pressure prevailing in the first and/or second fluid line and a control and evaluation unit for evaluating, inter alia, the pressure curve in time of the pressure measured by the pressure sensor arranged in the venous fluid line at least during shut-off of the first fluid line so as to detect herefrom an interruption or disturbance of the connection between the first connection means and the patient circulation, wherein the control and evaluation unit determines a variable representative of the pressure curve from the pressure curve, compares the representative variable to a reference value and, according to the result of the comparison, concludes the presence or absence of an interruption or disturbance of connection between the intracorporeal patient circulation and the blood treatment apparatus. It is preferred that the system according to aspects of the invention carries out the detection of the connection interruption and thus the blocking operation of the venous fluid line during the patient treatment without having to interrupt said treatment.

The system moreover includes a blood pump, wherein the pressure is measured for evaluating the pressure curve during a blood delivery operation of the blood pump (preferably without interruption of the patient treatment mode set in the treatment apparatus).

The first (venous) fluid line can be blocked and opened at regular or irregular time intervals.

According to a preferred embodiment of the invention, the pressure sensor is arranged in the first (venous) fluid line between the line shut-off and the first connection means, the representative variable is a mean value, median, minimum or maximum of the pressure curve, the reference value is a mean value, median, minimum or maximum of the pressure curve in the case of a non-existing interruption or disturbance of connection between the first connection means and the patient blood circulation, and the control and evaluation unit concludes the interruption or disturbance of connection if the representative variable deviates from the reference value by more than a predetermined amount.

The reference value preferably is the representative variable of a preceding pressure curve of the pressure measured by the pressure sensor during a previous shut-off of the fluid line.

In accordance with a further preferred embodiment of the invention, the pressure sensor is arranged in the first fluid line between the line shut-off and the first connection means, and the control and evaluation unit determines an approximated polynomial function, especially of the $1^{st}$ or $2^{nd}$ order, of the pressure curve, determines a measure of scale, especially variance or mean error, from deviations of individual values of the pressure curve from the approximated polynomial function as the representative variable and concludes the interruption or disturbance of connection if the representative variable deviates from the reference value by no more than a predetermined amount.

Preferably a predetermined time interval of the pressure curve at the beginning of the shut-off of the first fluid line is not taken into account for evaluation.

In accordance with a further preferred embodiment of the invention, the pressure sensor is arranged in the second fluid line, and the control and evaluation unit determines a frequency spectrum of the pressure curve, the representative variable being an amplitude, especially maximum amplitude, of a predetermined frequency range of the frequency spectrum which corresponds to a shut-off frequency of the first fluid line, and concludes the interruption or disturbance of connection if the representative variable deviates from the reference value by no more than a predetermined amount.

According to aspects of the invention, moreover a method for detecting an interruption of the connection between a blood treatment apparatus, especially dialyser, and a patient circulation, and especially for detecting an interruption of a venous connection between the blood treatment apparatus (dialyser) and the intracorporeal patient circulation, is provided, wherein the method includes the following: blocking a first, especially venous fluid line which is arranged between the blood treatment apparatus and a connection means (needle, cannula) with a line shut-off, measuring a pressure prevailing in the first venous fluid line and/or in a second, especially arterial fluid line arranged between the blood treatment apparatus and the patient circulation with respective pressure sensors, evaluating a pressure curve in time of the pressure measured by the pressure sensor at least during shut-off of the first fluid line so as to herefrom detect a (venous) interruption or disturbance of connection between the blood treatment apparatus and the patient circulation, the evaluation comprising the following steps of:

determining a variable representative of the pressure curve from the pressure curve, comparing the representative variable to a reference value, and concluding the presence or absence of a (venous-side) interruption or disturbance of connection between the blood treatment apparatus (dialyser) and the patient circulation corresponding to the result of comparison.

It is preferred that the pressure is measured for evaluation of the pressure curve during a blood delivery operation of a blood pump.

It is preferred that the first fluid line is blocked and opened at regular or irregular time intervals.

According to a preferred embodiment of the method of the invention, the pressure sensor is arranged in the first fluid line between the line shut-off and the first connection means (needle, cannula), the representative variable is a mean value, median, minimum or maximum of the pressure curve, the reference value is a mean value, median, minimum or maximum of the pressure curve in the case of a non-existing interruption or disturbance of connection between the first connection means and the patient circulation, and if the representative variable deviates from the reference value by more than a predetermined amount, the interruption or disturbance of connection is concluded.

The reference value can be the representative variable of a previous pressure curve of the pressure measured by the pressure sensor during a previous shut-off of the fluid line.

In accordance with a further preferred embodiment of the method according to aspects of the invention, the pressure sensor is arranged in the first fluid line between the line shut-off and the first connection means, and the step of evaluation comprises the following: Determining an approximated polynomial function, especially of the $1^{st}$ or $2^{nd}$ order, of the pressure curve, determining a measure of scale, especially variance or mean error, from deviations of individual values of the pressure curve from the approximated polynomial function as representative variable, and concluding the interruption or disturbance of connection if the representative variable deviates from the reference value by no more than a predetermined amount.

Accordingly, a predetermined time interval of the pressure curve at the beginning of the shut-off of the first fluid line is preferably not taken into account for evaluation.

In accordance with a further preferred embodiment of the method according to aspects of the invention, the pressure sensor is arranged in the second fluid line and the step of evaluating comprises the following: Determining a frequency spectrum of the pressure curve, the representative variable being an amplitude, especially maximum amplitude, of a predetermined frequency range of the frequency spectrum which corresponds to a blocking frequency of the first fluid line, and concluding the interruption or disturbance of connection if the representative variable deviates from the reference value by no more than a predetermined amount.

It is possible, according to aspects of the invention, to detect venous needle dislodgements (VND) or dislocations, as they are called. For example, due to movements of the patient or insufficient securing of the needle, the needle may get out of place or may even completely slip out of the puncture site. This is problematic especially in the area of the venous needle, as the blood is returned to the patient through this needle and the blood is correspondingly pressurized here. This may even further increase the risk of undesired dislocation or even slipping out of the needle.

In the present context, by the term of needle dislodgement both complete slip-out of the needle from the venous vascular access and only partial dislocation of the needle with restricted but still, to a certain extent, existing connection to the blood circulation are understood. When the needle only partially gets out of place, it can be located in the tissue surrounding the actual access site and cause perivascular hemorrhage there.

Hereinafter e.g. a system or an arrangement in which fluid taken from an object or a patient, e.g. blood, is guided in a secondary circulation outside the patient's body after passing a fluid treatment apparatus and subsequently is fed into the intracorporeal patient circulation again is referred to as "venous branch of the extracorporeal circulation". A system or an arrangement which takes a fluid (blood) from a patient's body and supplies it to the fluid treatment apparatus is referred to as "arterial branch of the extracorporeal circulation". The venous branch of the extracorporeal circulation can include, for example, a tube which returns the fluid taken from the object or patient and supplied to a treatment apparatus such as a purifying device or a dialyser from the treatment apparatus to the object or the patient, i.e. a tube which discharges the fluid and may also be in form of a blood discharge line of the dialyser.

Furthermore, according to aspects of the invention it is possible not only to identify an insufficient connection of a needle/cannula such as a venous needle or even slipping out of the needle of the provided access site on the patient, but also to detect e.g. a blood leakage in the venous branch downstream of the apparatus for identifying an interruption of the connection depending on the size of the blood leakage and/or the sensitivity of the sensor.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
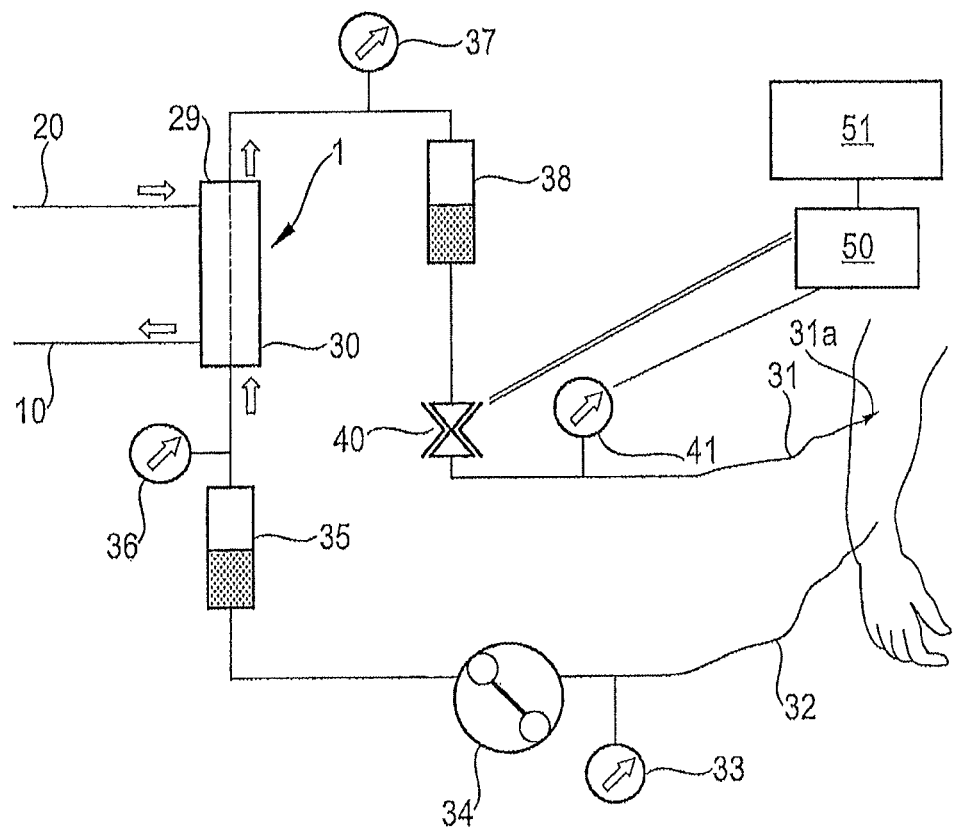
FIG. 1 shows an embodiment of a system according to aspects of the invention.

FIG. 1 illustrates an embodiment of a system according to aspects of the invention for detecting venous needle dislodgement. The embodiment shown in FIG. 1 of the system according to aspects of the invention for identifying a defective or missing venous connection between the extracorporeal blood circulation and the intracorporeal patient blood circulation is exemplified by way of a dialysis machine illustrated only schematically in FIG. 1.

Accordingly, FIG. 1 shows a dialyser 1 which is divided by a usually semipermeable membrane into a first chamber 29 arranged in a dialysis fluid path and a second chamber 30 which in turn is connectable/connected to the dialyser inlet via an (arterial) blood supply line 32 leading away from the patient blood circulation. The second chamber 30 is connectable/connected via a dialyser outlet including a (venous) blood discharge line 31 leading to the patient to the patient's blood circulation so as to supply the patient with the purified blood again. The first chamber 29 is connected to an intake 20 for fresh dialysis fluid and a drain 10 for used dialysis fluid.

Via a first pressure sensor 41 the venous pressure PV can be detected after clamping off a tube shut-off (tube shut-off clamp or tube clamp) 40 or similar flow shut-off means. The tube clamp 40 can be operated manually or automatically and can cause a complete or quasi complete shut-off of the fluid flow circuit back to the venous access of the patient. In the embodiment according to FIG. 1 the pressure sensor 41 for the venous pressure PV is disposed between the tube clamp 40 blocking the venous blood discharge line 32 and the venous patient access 31a and consequently is located in the blood return line to the patient. Since the pressure sensor 41 is arranged at the blood discharge line 31 directly ahead of the patient or in any case downstream of the tube clamp 40, substantially the pressure from the patient access is adjusted at the pressure sensor 41 in the case of proper connection to the patient circulation, whereas, if the needle has got completely or partly out of the patient access, the atmospheric pressure or the static pressure (after a particular period of time) is measured.

As is illustrated in FIG. 1, in the arterial branch or the blood supply line 32 of the extracorporeal blood circulation, i.e. in the branch leading from the patient to the dialyser inlet, a pressure sensor 33 for detecting the arterial pressure PA and a bubble collector 35 are arranged between which the blood pump 34 is arranged. A further pressure sensor 36 detects the pressure of the blood immediately at the dialyser inlet of the dialyser 1. The dialysis fluid is guided in the direction symbolized by the arrows via the dialysis fluid supply line 20 to the first chamber 29 of the dialyser 1 and from there via the dialysis fluid discharge line 10 to the outlet or drain. The blood to be purified flows through the second chamber 30 of the dialyser 1 and is guided at the dialyser outlet in the arrow direction to the blood discharge line (venous branch) 31.

In the blood discharge line 31 a further bubble collector 38 is preferably provided. A pressure sensor 37 detects the venous pressure PV in the blood discharge line 31 at the outlet of the dialyser 1.

The flow shut-off 40 which may also be in the form of a tube shut-off or tube shut-off clamp is provided, viewed in the blood flow direction, upstream of the pressure sensor 41 arranged at or in the blood discharge line 31. The blood supply line 32 and the blood discharge line 31 can be in the form of tubes, for example.

The flow rate of the blood circulation (extracorporeal) is controlled by the blood pump 34, wherein the second pressure sensor 33 for arterial pressure measurement is disposed at or in the blood supply line 32 upstream (viewed in the flow direction) of the blood pump 34.

When, as is provided according to aspects of the invention in the present preferred embodiment, the blood pump 34 is not stopped during the measurement for venous needle dislodgement, preferably in the line area between the blood pump 34 and the tube shut-off 40 a reservoir for receiving the delivered blood is provided. The delivered blood can also be received, for instance, by/in addition to the bubble collectors 38 and/or 35.

After the measurement for possible needle dislodgment, the blood intermediately stored in the bubble collector 38 and/or 35 can be returned to the patient again after opening the tube shut-off 40 so that the storage volume of the bubble collector 38 is available again for receiving blood during subsequent measurement.

For this purpose, a level regulation may be provided in the storage volumes of the bubble collectors 38 and/or 35 so that the level of the amount of fluid stored in the bubble collectors 38 and/or 35 is regulated to a desired level when the tube shut-off 40 is opened.

A control means, e.g. in the form of a data processing and storage unit (control and evaluating unit) 50 controls a (necessary) part of or all elements illustrated in FIG. 1 via proper interfaces, wherein in FIG. 1 only the connection to the pressure sensor 41 and to the tube shut-off 41 is shown. In particular, the data processing and control unit 50 also controls the arterial pressure sensor 33 when used according to aspects of the invention. The data processing and storage unit 50 collects information also about other parameters of the dialysis apparatus, e.g. blood flow, dialysis fluid flow and/or treatment period. These parameters are processed together with the data measured. The data processing and storage unit 50 serves for processing the measured pressure values as well as for controlling the blood shut-off and the measuring times. Furthermore one or more internal or external storage units can be provided for storing measuring values, calculated values and/or intermediate values, results etc. as well as the control procedures.

The measuring values from the pressure sensors 33, 36, 37 and 41 are transmitted via data communications, which may be cable-bound and/or wireless, to the data processing and storage unit 50 which is in the form of a data processing and evaluation unit so as to identify venous needle dislodgements (VND).

Moreover an output unit 51 in the form of a warning signal unit or display is optionally provided which is connected to the data processing and storage unit 50 via a cable-bound or wireless data communication. The output unit 51 outputs an optical and/or acoustic warning signal and/or a text for explaining a problem on a display, for instance, when malfunction of the dialysis machine and/or the apparatus for detecting needle dislodgement, especially venous needle dislodgement, is detected and/or when needle dislodgement is detected. Moreover, the output unit 51 can be configured for optical, acoustic or electronic output or an output in any other form, for example in the form of an electronic storage, a print, an e-mail transmission or the like.

Even if it is not shown in FIG. 1, furthermore one or more additional measuring means, pumps, bubble collectors, air detectors, shut-off clamps etc., which are not shown, can be provided as needed.

Figure 2:
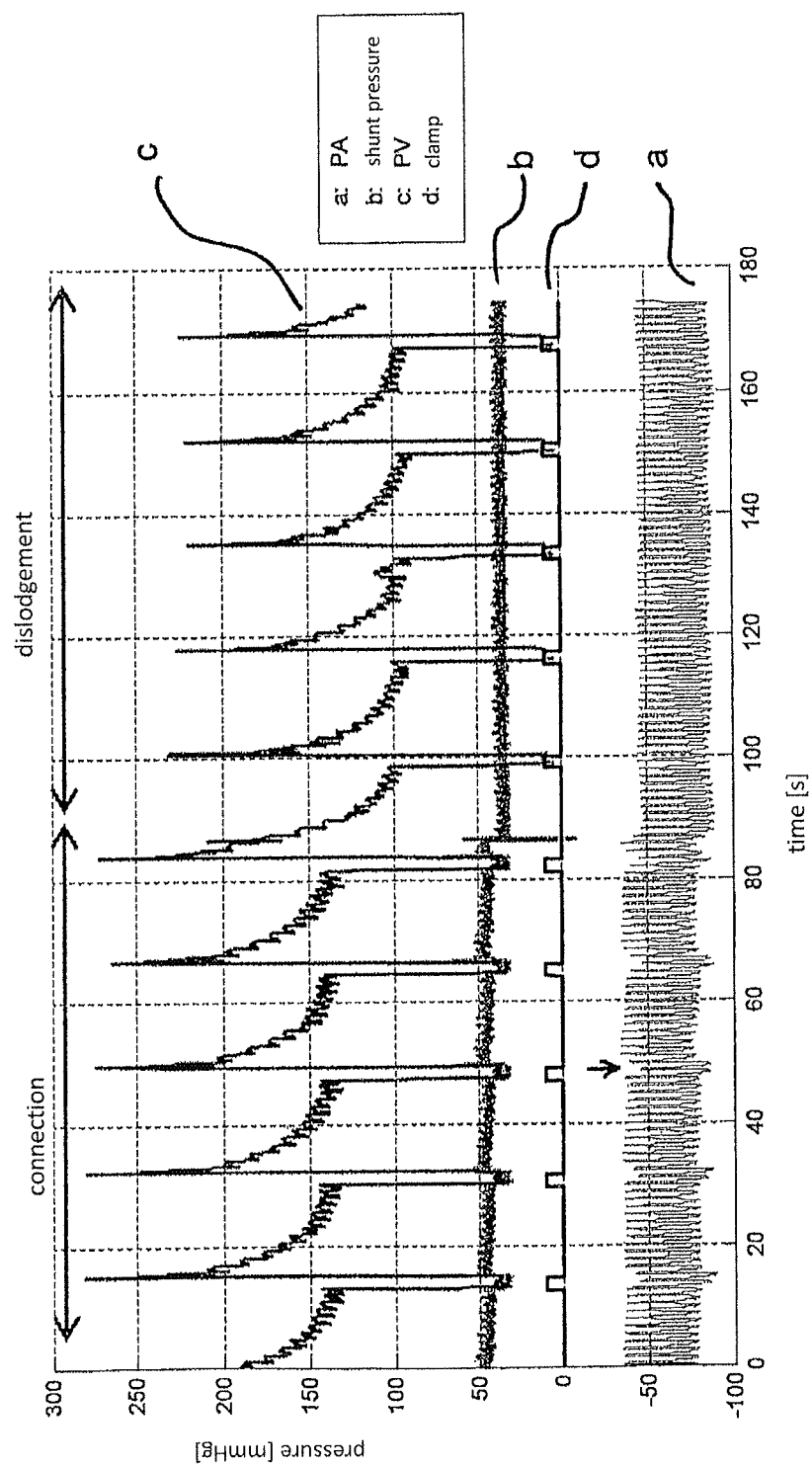
FIG. 2 shows a diagram of the pressure curves in time of the arterial pressure (a), the shunt pressure (b) and the venous pressure (c) as well as the clamp closing and opening curve in time (d) before (connection) and after (disconnection) a needle dislodgement.

FIG. 2 illustrates an example of the pressure curves in time of the arterial pressure PA measured by the (arterial) sensor 33 (curve a), the shunt pressure (curve b) and the venous pressure PV measured by the (venous) sensor 41 (curve c) as well as of the clamp closing and opening curve of the shut-off or clamp 40 (curve d) before and after VND. According to a preferred embodiment, the clamp 40 is regularly closed for a short period of time, for example 2 seconds. The pressure PV of the sensor 41 absorbed during this period is dependent on the shunt pressure of the patient in the case of connection. In the case of disconnection it corresponds to the static pressure which is adjusted by the difference in height between the sensor and the cannula.

Since, according to a preferred embodiment, the blood pump 34 and thus also the therapy are not stopped during closure of the clamp in accordance with the invention, but the delivered blood cannot be returned to the patient, a congestion of the blood in the dripping chamber 38 and/or 35 occurs which relieves again after opening the clamp 40, however. From FIG. 2 it is evident that corresponding to the illustrated pressure curve of the arterial pressure PA in the arterial blood line no blood is congested. Furthermore, in FIG. 2 a difference in the pressure curve in the case of needle connection compared to needle dislodgement can be clearly inferred from the course of the curve c.

Figure 3:
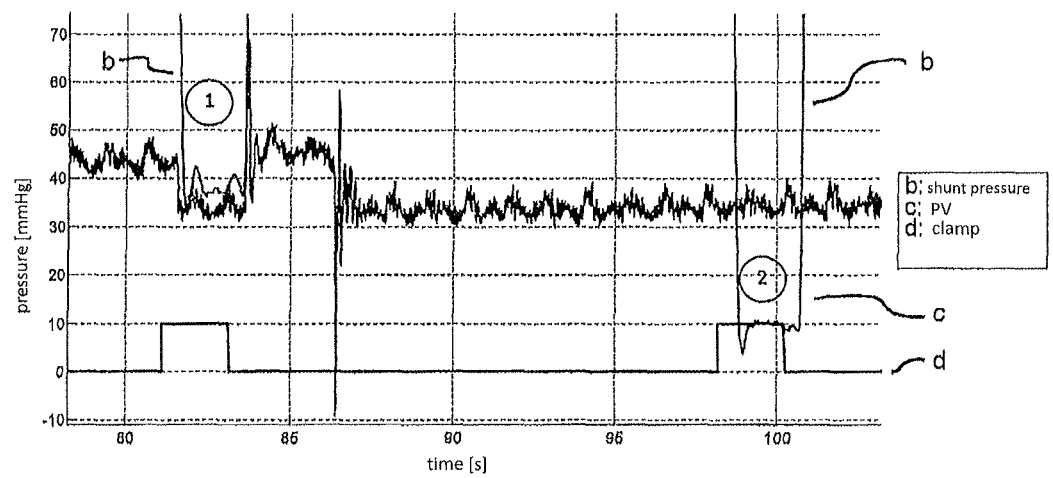
FIG. 3 shows an enlarged cutout from the diagram of FIG. 2.

Consequently, FIG. 2 shows a typical pressure curve, when the system or method according to aspects of the invention is used, for an exemplary closing time of 2 seconds and an exemplary opening time of 15 seconds of the clamp 40 (i.e. a clamp period of 17 seconds). Five clamp closures are shown for each connection and disconnection. As is clearly evident even by way of FIG. 3 showing a cutout of FIG. 2, the pressure PV decreases as soon as the clamp 40 is closed in the case of connection (cf. encircled 1 in FIG. 3) to a level approximately corresponding to the shunt pressure. After opening the clamp 40, the volume spanned ahead of the clamp 40 is relieved, thus the pressure PV suddenly increases and slowly decreases to a balanced state or to the moment at which the clamp 40 is closed again. In the case of disconnection (cf. encircled 2 in FIG. 3), however, the pressure PV decreases to a lower level corresponding to the static pressure. Hence, from a difference between the two levels VND can be concluded.

In accordance with a first embodiment according to aspects of the invention, thus a value w (e.g. mean value, median, minimum, maximum etc.) of the pressure curve of PV is formed over a closing time of the clamp (e.g. 2 seconds) which represents the level of PV. The value w established at the beginning of the measurements or at the beginning of the treatment is used as reference value Rw, for example. The reference value Rw can also be formed (updated) newly each time from the current value w or from a different previous value w and can be used as reference value Rw for the value w of the next clamp closure. Upon each re-closure of the clamp or following each re-closure of the clamp the current value w is compared to the reference value Rw. For instance, a difference $\Delta w$ between the current value w and the reference value Rw, preferably $\Delta w = |w - Rw|$, is calculated. When the difference $\Delta w$ exceeds a predetermined (first) threshold or limit, VND is concluded. In other words, VND is concluded when the current value w deviates from the reference value Rw by more than a predetermined amount.

If the process is continued after detecting VND (without eliminating the same), preferably the value w deviating from the reference value Rw by more than the predetermined amount is not used for updating the reference value Rw, when the difference $\Delta w$ exceeds the predetermined threshold or limit and the reference value Rw is updated in each case as afore-described. Instead, the current reference value or a different previous reference value can be used as new reference value.

By continuation of the process, even if VND has been detected, the result of detection of VND can be confirmed or determined to be faulty by way of one or more further values w of subsequent clamp closures, for example.

However, the value w which deviates from the reference value Rw by more than the predetermined amount can also be used instead or additionally as further reference value Rw', when the process is continued. If then the next value w is compared to the new reference value Rw' and the absolute value of the difference $\Delta w' = w - Rw'$ between the two does not exceed a second threshold or limit which is less than the first threshold or limit, the detection of VND can be confirmed. Otherwise, for example an error of detecting the VND can be concluded which may be due to a movement of the patient, for instance.

Figure 4:
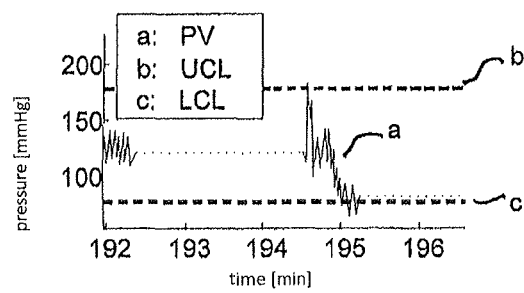
FIG. 4 shows a diagram of the venous pressure curve in time before and after a movement of the patient.

The venous pressure may strongly vary during a therapy due to a patient's movements. Movements of a patient which influence the venous pressure may be the patient lifting or lowering his/her punctured arm or else the patient lying down or sitting up. FIG. 4 shows an example of a venous pressure variation that can be traced back to a patient's movement. In the example the pressure difference or pressure change amounts to approximately 40 mmHg which corresponds to a vertical change of position of 50 cm.

Figure 5:
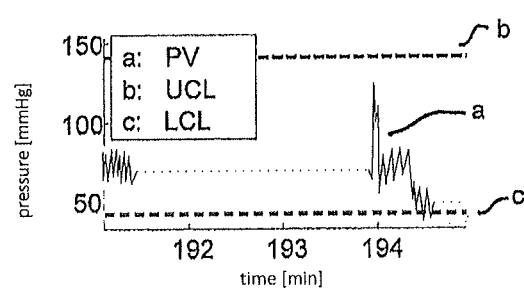
FIG. 5 shows a diagram of the venous pressure curve in time before and after needle dislodgement.

In the case of VND the venous pressure is reduced by the shunt pressure. The physiological shunt pressure is approximately between 15 and 45 mmHg, thus a maximum pressure difference of about 45 mmHg can be expected. FIG. 5 exemplifies the course of a venous pressure with a change of pressure by reason of VND. The pressure drop in that case amounts to approximately 25 mmHg.

The data on which the diagrams of the FIGS. 4 and 5 are based were established by experiments on a test stand imitating the human shunt circulation. Water was used as blood substitute. The inserted upper and lower limits UCL and LCL (DIN VDE 0753-4) correspond to the limits calculated during the therapy by the dialysis machine.

It is evident from FIGS. 4 and 5 that the detection of VND (pressure drop <45 mmHg) poses a challenge because of the pressure variations during a dialysis therapy. In practice frequently false alerts are triggered by reason of movements of the patients (or else changes of parameters such as ultrafiltration rate UFR, dialysis fluid flow DF or level regulation LR that influence the venous pressure but are not taken into account, for instance, when the limits UCL and LCL are calculated). Moreover, frequently VND are detected late or are not detected at all, as the lower limit LCL is not underrun due to a too small pressure difference.

Figure 6:
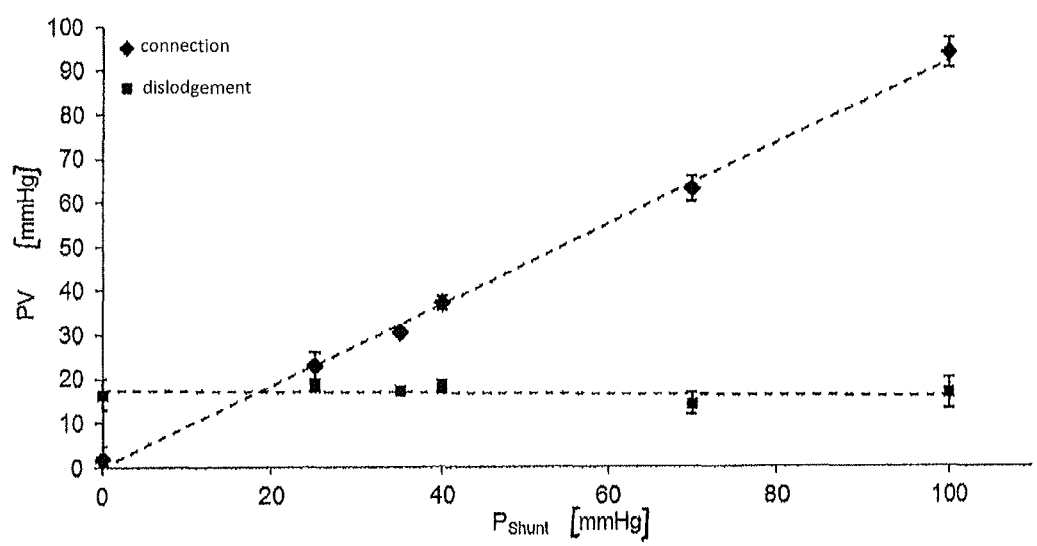
FIG. 6 shows a diagram of the final level of the venous pressure for different shunt pressures in the case of disconnection and connection.

The remaining static pressure in the case of disconnection, which is dependent on the position of the sensor and the cannula, is about 10 to 20 mmHg (also other pressure values are possible, if the cannula falls to the ground). As is apparent from FIG. 6 illustrating a diagram of the final level of the venous pressure for different shunt pressures for each of dislodgement and connection, a clear distinction between connection and dislodgement can become difficult for patients with low shunt pressures already from a shunt pressure of 25 mmHg (and less) even by the foregoing method according to the first embodiment.

When comparing the venous pressure curves PV with a closed clamp in the case of connection and dislodgement (1=connection; 2=dislodgement) in FIG. 3 it is obvious that they are different not only as to their level but also as to their curve. Both pressure curves with a closed clamp include a first "system-related" minimum which is generated due to the sudden pressure drop (flow of blood out of the cannula) and is dependent on the blood properties (e.g. viscosity) and the cannula diameter. After this system-related minimum has subsided, the course in the case of dislodgement (2) then describes an approximated straight line or a slightly bent curve, whereas the course in the case of connection (1) shows slight pulsation or vibration. This pulsation is caused by the blood pump. The pulsation of the arterial pressure generated by the blood pump is transmitted via the arterial patient connection to the shunt pressure (patient) and from there via the venous patient connection to the venous pressure PV. Thus the pulsation can also be perceived, in a strongly dampened manner, in the pressure curve of PV. This pulsation can be detected irrespective of movements of the patient, as the level (constant component) of the pressure PV itself is irrelevant to the detection.

According to a second embodiment of the invention, therefore the pressure curve with a closed clamp is approximated by a polynomial function, preferably of the $1^{st}$ or $2^{nd}$ order. This can be effectuated, for example, by polynomial regression (correspondingly of the $1^{st}$ or $2^{nd}$ order).

Subsequently, a variance or a mean error, for instance, is established from the deviations of the pressure values used from the approximated polynomial function by calculating a mean value of the deviations. Alternatively, a mean square error or mean higher-order error can be calculated from the deviations.

Figure 7:
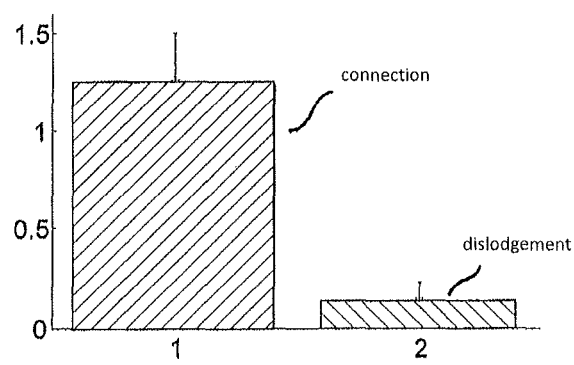
FIG. 7 shows a diagram of the mean error with its standard deviation from a proximity function of the venous pressure curve in the case of connection (1) and disconnection (2)

FIG. 7 exemplifies a mean error for the PV pressure curve for connection (1) and dislodgement (2) and the associated standard deviation (vertical line). The mean error in the case of connection amounts to about 1.25 and the mean error in the case of dislodgement amounts to only about 0.2. It becomes clear herefrom that the mean error in the case of connection is definitely greater compared to the mean error in the case of dislodgement. This is due to the fact that a polynomial function of the $1^{st}$ or $2^{nd}$ order properly approximates the PV pressure curve with a closed clamp in the case of dislodgement but not in the case of connection.

The error calculated in the foregoing manner, e.g. the mean error, is then compared to a threshold or limit. If the error is smaller than the threshold, VND is concluded. In the foregoing case of FIG. 7, the threshold can amount to e.g. 0.3. Other useful values which are properly established by experiments and/or simulations and with which a reliable distinction can be made between the afore-calculated error of the PV pressure values in the case of connection and in the case of dislodgement are also possible.

For calculating the polynomial function preferably the afore-mentioned system-related minimum is left aside. For this purpose, for example the values of the PV pressure curve at the beginning with a closed clamp, i.e. in the first seconds, e.g. 0.6 seconds, are not applied. This period at the beginning (equally depending on the blood flow and the selected needle/cannula size) can be determined in response to the total clamp closing time and/or the clamp closing/opening period.

Now FIG. 2, especially the curve of the arterial pressure PA shown there, shall be contemplated again. When the arterial pressure PA is compared before (connection) and after (dislodgement) VND (at about 86 s), it becomes clear that the pressure PA (upper envelope and lower envelope) somewhat decreases before VND with each clamp closure and after that increases again (cf. arrow at about 50 s), whereas it is almost constant in the case of dislodgement. The effect of decrease is caused by the fact that the shunt flow is reduced due to the clamp closure (blood continues to be withdrawn at about 300 ml/min, but is not returned again) and thus the shunt pressure equally decreases. Since the arterial pressure is composed, just as the venous pressure, of the shunt pressure and a pressure component generated by the blood pump, the pressure drop of the shunt pressure is transmitted to the arterial pressure. The superimposed variation or vibration generated in this way renders the connection (existing variation or vibration) distinguishable from the dislodgement (non-existing variation or vibration).

Figure 8:
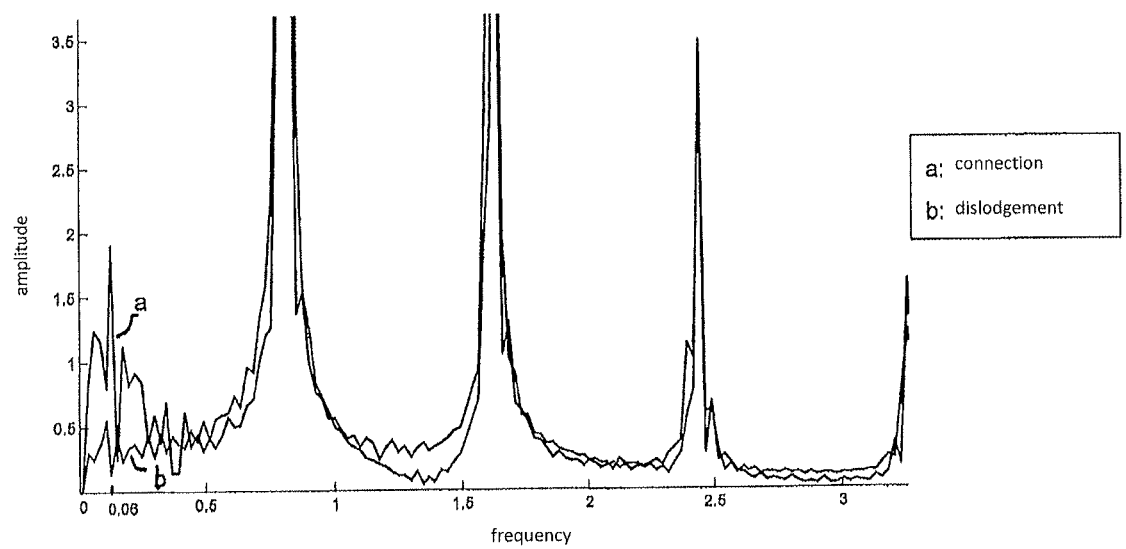
FIG. 8 shows a frequency spectrum of the arterial pressure for connection and disconnection.

In accordance with a third embodiment of the invention, therefore a spectral analysis of the PA pressure curve measured for the period of the closed clamp and a particular period of time exceeding the former is carried out. For this purpose, a fast Fourier transformation FFT is carried out, for example. However, also other frequency analysis methods are possible. FIG. 8 illustrates one example of a result of such FFT of the PA pressure curve with a closed clamp in the case of connection and in the case of dislodgement.

The main maximum at 0.8 Hz shown there (and its harmonic multiples) are due to the rotation of the blood pump. Since in the present example the clamp was closed every 17 seconds, an additional maximum exists at about 0.06 Hz in the case of connection (curve a). In the case of dislodgement (curve b) this maximum does not exist. Hence a clear distinction between the two states of connection and dislodgement is possible.

In accordance with the third embodiment, a frequency range is fixed around the closing frequency fs of the clamp, for example fs ±c×fx (in the present example 0.06 Hz ±0.5×0.06 Hz), wherein c is an appropriately selected constant so that a frequency corresponding to the dissolution of the frequency spectrum of the closing frequency to be detected is contained and can be detected. Then, for instance, maximum amplitude is established in this frequency range of the FFT curve. This amplitude is then compared to an amplitude threshold or limit. If this maximum amplitude falls below the amplitude threshold, VND is concluded. The amplitude threshold is determined by experiences obtained from experiments so that a reliable distinction is possible between connection and dislodgement by way of the frequency spectrum, i.e. as a threshold which is most safely exceeded by the maximum amplitude in the case of connection but which is not exceeded by the corresponding amplitudes in the case of dislodgement. The amplitude threshold for the example illustrated here amounts to 1.1, for example.

The foregoing methods according to the first, second and third embodiments are not mutually exclusive and can be combined with each other in any way so as to improve the reliability of the detection of VND. For example, the result of a method according to aspects of the invention (presence or absence of VND) can be confirmed or dismissed by another method according to aspects of the invention. It is of advantage when the combined methods are simultaneously implemented so as to arrive at a reliable result as quickly as possible. This is possible as the same structure as described by way of FIG. 1, for example, can be used.

Summing up, the described system and machine control method serves for detecting an interruption of the connection between a blood treatment apparatus and a patient blood circulation which can be connected to the blood treatment apparatus via a first connection means adapted to be attached to a first fluid line, comprising a line shut-off for blocking the first fluid line arranged between the blood treatment apparatus and the connection means, a second fluid line arranged between the blood treatment apparatus and the patient blood circulation, a pressure sensor arranged in the first fluid line or the second fluid line for measuring the pressure prevailing in the first or second fluid line, and a control and evaluation unit for evaluating the pressure curve in time of the pressure measured by the pressure sensor during shut-off of the first fluid line so as to detect herefrom an interruption or disturbance of the connection between the first connection means and the patient blood circulation, wherein the control and evaluation unit determines a variable representative of the pressure curve from the pressure curve, compares the representative variable to a reference value and, corresponding to the result of the comparison, concludes the presence or absence of an interruption or disturbance of the connection between the first connection means and the patient blood circulation.

The invention claimed is:

1. A system for detecting an interruption of the connection between an extracorporeal blood treatment apparatus and an intracorporeal patient blood circulation to which the extracorporeal blood treatment apparatus is connectable or connected via a fluid connection means that is attachable or attached to a venous fluid line and via an arterial fluid line, comprising:
   a line shut-off for blocking the venous fluid line arranged between the blood treatment apparatus and the fluid connection means;
   at least one blood pump arranged in the arterial fluid line configured for continuous blood delivery during blocking of the venous fluid line by the line shut-off;
   at least one pressure sensor arranged in at least one of the venous fluid line or the arterial fluid line for measuring the pressure prevailing in the at least one of the venous fluid line or the arterial fluid line;
   a control and evaluation unit adapted to evaluate a pressure curve in time of the pressure measured by the at least one pressure sensor during blocking of the venous fluid line to detect an interruption or disturbance of the connection between the fluid connection means and the patient blood circulation, for which the control and evaluation unit is configured;
      to determine a variable representative of the pressure curve from the pressure curve;
      to compare the representative variable to at least one of a stored reference value or range of reference values; and
      to conclude the presence or absence of an interruption or disturbance of the connection of the venous fluid line between the blood treatment apparatus and the patient circulation as a result of the comparison.

2. The system according to claim 1, wherein the venous fluid line is blocked and opened at regular or irregular time intervals.

3. The system according to claim 1:
   wherein one of the at least one pressure sensor is arranged in the venous fluid line between the line shut-off and the fluid connection means;
   the representative variable is a mean value, median, minimum or maximum of the pressure curve;
   the reference value is a mean value, median, minimum or maximum of the pressure curve in the case of a non-existing interruption or disturbance of the connection between the fluid connection means and the patient circulation; and
   the control and evaluation unit concludes an interruption or disturbance of the connection, if the representative variable deviates from the reference value by no more than a predetermined amount.

4. The system according to claim 3, wherein the reference value is the representative variable of a previous pressure curve of the pressure measured by the one of the at least one pressure sensor during a previous blocking of the venous fluid line.

5. The system according to claim 1, wherein:
the pressure sensor is arranged in the venous fluid line between the line shut-off and the fluid connection means; and
the control and evaluation unit:
  determines an approximated polynomial function of the pressure curve;
  determines a measure of scale from deviations of individual values of the pressure curve from the approximated polynomial function as the representative variable; and
  concludes an interruption or disturbance of the connection, if the representative variable deviates from the reference value by no more than a predetermined amount.

6. The system according to claim 5, wherein a predetermined time interval of the pressure curve at the beginning of blocking of the venous fluid line is not taken into account for evaluation.

7. The system according to claim 1, wherein:
one of the at least one pressure sensor is arranged in the arterial fluid line; and
the control and evaluation unit:
  determines a frequency spectrum of the pressure curve, the representative variable being an amplitude, especially maximum amplitude, of a predetermined frequency range of the frequency spectrum which corresponds to a frequency of blocking of the venous fluid line; and
  concludes an interruption or disturbance of the connection, if the representative variable deviates from the reference value by no more than a predetermined amount.

8. A machine control method for detecting an interruption of the connection between an extracorporeal blood treatment apparatus and an intracorporeal patient blood circulation to which the extracorporeal blood treatment apparatus is connectable or connected via a fluid connection means, attachable or attached to a venous fluid line and via an arterial fluid line, the machine control method comprising the following steps of:
blocking the venous fluid line arranged between the blood treatment apparatus and the connection means by means of a line shut-off;
measuring a pressure prevailing in at least one of the venous fluid line or the arterial fluid line arranged between the blood treatment apparatus and the patient blood circulation by at least one pressure sensor, wherein at least one blood pump, which is operated for continuous blood delivery during blocking of the venous fluid line by the line shut-off, is arranged in the arterial fluid line;
evaluating a pressure curve in time of the pressure measured by the at least one pressure sensor during blocking of the venous fluid line to detect an interruption or disturbance of the connection at least between the fluid connection means and the patient circulation, wherein the evaluation comprises the steps of:
  determining a variable representative of the pressure curve from the pressure curve;
  comparing the representative variable to at least one of a reference value or reference value range; and
  concluding the presence or absence of an interruption or disturbance of the connection between the fluid connection means and the patient circulation corresponding to the result of the comparison.

9. The method according to claim 8, wherein the pressure for evaluating the pressure curve is measured during blood delivery operation of a blood pump.

10. The method according to claim 8, wherein the venous fluid line is blocked and opened at regular or irregular time intervals.

11. The method according to claim 8, wherein:
one of the at least one pressure sensor is arranged in the venous fluid line between the line shut-off and the connection means;
the representative variable is a mean value, median, minimum or maximum of the pressure curve;
the reference value is a mean value, median, minimum or maximum of the pressure curve in the case of a non-existing interruption or disturbance of the connection between the fluid connection means and the patient circulation; and
an interruption or disturbance of the connection is concluded, if the representative variable deviates from the reference value by no more than a predetermined amount.

12. The method according to claim 11, wherein the reference value is the representative variable of a previous pressure curve of the pressure measured by the one of the at least one pressure sensor during a previous blocking of the venous fluid line.

13. The method according to claim 8, wherein:
the pressure sensor is arranged in the venous fluid line between the line shut-off and the fluid connection means; and
the step of evaluation comprises:
  determining an approximated polynomial function of the pressure curve;
  determining a measure of scale from deviations of individual values of the pressure curve from the approximated polynomial function as representative variable; and
  concluding an interruption or disturbance of the connection, if the representative variable deviates from the reference value by no more than a predetermined amount.

14. The method according to claim 13, wherein a predetermined period of time of the pressure curve at the beginning of the blocking of the venous fluid line is not taken into account for evaluation.

15. The method according to claim 8, wherein:
one of the at least one pressure sensor is arranged in the arterial fluid line; and
the step of evaluation comprises:
  determining a frequency spectrum of the pressure curve, the representative variable being an amplitude of a predetermined frequency range of the frequency spectrum which corresponds to a frequency of blocking of the venous fluid line; and
  concluding the interruption or disturbance of the connection, if the representative variable deviates from the reference value preferably by no more than a predetermined amount.

* * * * *